US005541152A

United States Patent [19]
Lehs

[11] Patent Number: 5,541,152
[45] Date of Patent: Jul. 30, 1996

[54] HERBICIDE AND FERTILIZER COMPOSITION AND METHOD OF USING SAME

[75] Inventor: David J. Lehs, Independence, Iowa

[73] Assignee: Platte Chemical Company, Greeley, Colo.

[21] Appl. No.: 294,000

[22] Filed: Aug. 19, 1994

[51] Int. Cl.⁶ .................................................. A01N 25/32
[52] U.S. Cl. ............................................................ 504/110
[58] Field of Search ............................................. 504/110

[56] References Cited

U.S. PATENT DOCUMENTS

| Re. 31,455 | 12/1983 | Bayer | 562/435 |
|---|---|---|---|
| 3,854,923 | 12/1974 | Ott | 21/64 |
| 3,909,229 | 9/1975 | Ott | 71/64 |
| 3,997,319 | 12/1976 | Ott | 71/27 |
| 4,352,688 | 10/1982 | Ott | 71/11 |
| 4,394,506 | 7/1983 | Levitt | 544/321 |
| 4,481,029 | 11/1984 | Levitt | 544/212 |
| 4,547,215 | 10/1985 | Wolf | 544/321 |
| 4,629,493 | 12/1986 | Ura et al. | 544/354 |

OTHER PUBLICATIONS

"Asset" promotional video, ©on or before 1993, Helena Chemical Company, Memphis, Tennessee.
Label, "ACA Concentrate® 15–0–0, No. 34155," publ. Jan. 1992, Platte Chemical Co., Fremont, NE.
Label, "ACA Concentrate® 15–0–0, No. 34133," publ. Jan. 1992, Platte Chemical Co., Fremont, NE.
Label, "ACA Concentrate® 15–0–0, (Wisconsin)—No. 32292," publ. Jan. 1992, Platte Chemical Co., Fremont, NE.
Label, "ACA Concentrate® 15–0–0 Material Safety Data Sheet," publ. Jan. 1992, Platte Chemical Co., Fremont, NE.
"The ABC's of Spraying," publ. May 1993, Loveland Industries, Inc., Greeley, Colorado.
"ACA® Concentrate+N–Serve* Anhydrous Program" brochure, publ. on or before Sep. 1992, Grower Service Corp., Terre Haute, Indiana.
"ACA® Concentrate+N–Serve* Fall Anhydrous Program" brochure, publ. on or before Sep. 1992, Grower Service Corp., Terre Haute, Indiana.
"ACA® Concentrate Wheat Program" brochure, publ. on or before Sep. 1993, Grower Service Corp., Terre Haute, Indiana.
"RENU Nitrogen–Zinc Plant Nutrient Solution" label, publ. on or before Jan. 1993, T–Tech Corp., Chester, Virginia.
"Model 1005 Dispensing System" brochure, publ. on or before Jan. 1993, Economy Controls Corporation, St. Louis, Missouri.
"Help Your Crops Achieve Full Yield Potential–Ask for ACA® Concentrate" brochure, publ. on or before Jan. 1993, United Agri Products, Inc., Greeley, Colorado.
"ACA Impregnation System" brochure, publ. Jan. 26, 1993, Grower Service Corp., Terre Haute, Indiana.
"Increase Corn Yields Over the Winter" brochure, publ. on or before Jan. 1993, Midwest Valley Chemical, Wall Lake, Iowa.
"ACA Salesman Handbook", pp. 1–39, publ. on or before Nov. 1991, United Agri Products, Inc., Greeley, Colorado.
"Asset Plant Root Stimulator" label, publ. on or before Nov. 1992, Setre Chemical Co., Memphis, Tennessee.
"Asset Plant Root Stimulator" brochure, publ. on or before Nov. 1992, Setre Chemical Co., Memphis, Tennessee.
"Asset Results—1990 (Eastern Iowa)", *Helena Agri–Dealer*, publ. on or before Jul. 1992, Helena Chemical Company, Memphis, Tennessee.
"Root Stimulator Improves Standability Yield, Health Of soybean Crops ion Midwest", *Helena Agri–Dealer*, publ. on or before Jul. 1992, Helena Chemical Company, Memphis, Tennessee.
"Difference In Roots Stems From Asset", *Helena Agri–Dealer*, publ. on or before Jul. 1992, Helena Chemical Company, Memphis, Tennessee.

*Primary Examiner*—Richard L. Raymond
*Assistant Examiner*—Brian G. Bembenick
*Attorney, Agent, or Firm*—Carol W. Burton, Esq.; Holland & Hart, LLP

[57] ABSTRACT

A composition containing an effective amount of a herbicide and an aqueous ammoniacal ionic solution of metal alkanoates is disclosed. Alkanoates having from 2 to 6 carbon atoms are preferred, with acetates most preferred. Metals selected from the group consisting of boron, calcium, copper, iron, magnesium, manganese, molybdenum, potassium, sodium and zinc are preferred, with zinc particularly preferred. Both broadleaf and grass herbicides are preferred, with herbicides having an active ingredient selected from the group consisting of quizalofop, sodium salt of bentazon, sodium salt of acifluorfen, chlorimuron ethyl, lactofen, fluazifop-p-butyl, fenoxaprop-ethyl, methyl 3-[[[[4-methoxy-6-methyl-1,3,5-triazin-2-yl]amino]carbonyl]amino]sulfonyl]2-thiophenecarboxylate, 2-[1-ethoxyimon]butyl]-5-[2-[ethylthio]propyl]-3-hydroxy-2-cyclohexene-1-one, and ammonium salt of imazethapyre. The composition of the present invention is applied postemergence to crops using conventional broadcast spray techniques.

17 Claims, No Drawings

HERBICIDE AND FERTILIZER COMPOSITION AND METHOD OF USING SAME

FIELD OF THE INVENTION

This invention relates to herbicide and fertilizer compositions and methods of treating crops therewith.

BACKGROUND OF THE INVENTION

Herbicides are applied to crops and to the soil in which crops are to be grown to prevent or control the growth of weeds. When applied postemergence to crops, herbicides are often applied using conventional pressure broadcast spray methods. Commonly used commercial herbicides which may be broadcast sprayed are listed in Table I:

TABLE I

| Herbicide | Source | Active Ingred. | Class |
|---|---|---|---|
| Assure II ™ | Du Pont | quizalofop | grass herbicide |
| Basagran ™ | BASF | sodium salt of bentazon | broadleaf herbicide |
| Blazer ™ | BASF | sodium salt of acifluorfen | broadleaf herbicide |
| Classic ™ | Du Pont | chlorimuron ethyl | broadleaf herbicide |
| Cobra ™ | Valent Co. | lactofen | broadleaf herbicide |
| Fusion ™ | Zeneca | fluazifop-p-butyl and fenoxaprop-ethyl | grass herbicide |
| Galaxy ™ | BASF | sodium salts of bentazon and acifluorfen | broadleaf herbicide |
| Pinnacle ™ | Du Pont | methyl 3-[[[[4-methoxy-6-methyl-1,3,5-triazin-2-yl]amino]carbonyl]amino]sulfonyl]2-thiophenecarboxylate | broadleaf herbicide |
| Poast Plus ™ | BASF | 2-[1-ethoxyimino]butyl]-5-[2-[ethylthio]propyl]-3-hydroxy-2-cyclohexene-1-one | grass herbicide |
| Pursuit ™ | American Cyanamid | ammonium salt of imazethapyr | grass/broadleaf herbicide |

Further data about the above-listed herbicides are available in the following U.S. patents and U.S. Environmental Protection Agency registrations: Assure II™—U.S. Pat. No. 4,629,493; Basagran™—U.S. Pat. No. Re. 31,455 and E.P.A. Reg. No. 7969- 45; Blazer™—E.P.A. Reg. No. 7969-79; Classic™—U.S. Pat. Nos. 4,394,506 and 4,547, 215; Cobra™—E.P.A. Reg. 59639-34; Fusion™—E.P.A. Reg. No. 10182-343; Galaxy™—E.P.A. Reg. No. 7969-77; Pinnacle™—U.S. Pat. No. 4,481,029; Poast Plus™—E.P.A. Reg. No. 7969-88; and Pursuit™—E.P.A. Reg. No. 241-310.

Application of postemergence herbicides can, however, have a deleterious effect not only on undesirable weeds but also on the primary crop. For example, when herbicides are broadcast, the leaves of the primary crop can burn, shrivel or discolor. This damage can be extensive, sometimes damaging over 40% of the leaves of the plants of the crop. In addition to giving the crops a poor cosmetic appearance, plant growth can be stunted. Even when plant growth is not permanently stunted and subsequent new leaf growth replaces the injured leaves and restores the plants to optimum growth rates, during the time period the plant leaves are damaged, transpiration efficiency can be effected, plants can be weakened and growth phases can be retarded. These problems have not heretofore been fully addressed.

Fertilizers and plant additives are also commonly applied to the soil in which crops are to be grown and to the soil after plants have emerged from the soil. For example, aqueous ammoniacal ionic solutions of alkanoates having from two to six carbon atoms have proven effective in stimulating plant growth in corn, soybeans, wheat and other crops. Metal ammonium alkanoates have proven especially effective, with agriculturally acceptable metals selected from the group consisting of boron, calcium, copper, iron, magnesium, manganese, molybdenum, potassium, sodium and zinc preferred.

More particularly, U.S. Pat. No. 4,352,688 for "Nitrogen Fertilizers" to Ott teaches that low molecular weight alkanoic acids and alkanoate anions thereof, particularly acetic acid and acetate ions, effectively promote plant growth and yield by enhancing the ability of nitrogen fertilizers. U.S. Pat. No. 3,909,229 for "Plant Nutrients" to Ott teaches aqueous ammoniacal ionic solutions of zinc carboxylates, for example zinc acetate in combination with ammonia, as effective fertilizers. U.S. Pat. No. 3,997,319 for "Fertilizing Method" to Ott teaches the application of substantially anhydrous liquid ammonia containing an ionic solution of a zinc carboxylate to soil below the surface of the soil, in order to supply zinc and nitrogen to plants growing in the soil.

Substantially anhydrous liquid ammonia is typically injected below the soil surface, under pressure. Anhydrous liquid ammonia is typically applied in fall—after the end of the growing season, in early spring—prior to planting, or in late spring—post-emergence, i.e. after a crop has germinated and leafed out. While ammonium nitrogen is readily assimilated by plants and thus liquid anhydrous ammonia is a preferred fertilizer, the aforementioned method is avoid when wet soil or windy weather conditions prevail. When weather conditions are unsuitable, growers may skip scheduled early spring, late spring or fall applications of anhydrous liquid ammonia. When this occurs, crop yields may be reduced. Moreover, for any aqueous ammoniacal ionic solutions of metal alkanoates or other crop additives which were to be applied with anhydrous ammonia, a missed application of anhydrous ammonia also results in a missed application of the crop additive.

In some cases the liquid fertilizer which functions as a carrier for the aqueous ionic solution of metal alkanoates plant additive solution may be broadcast to the soil in a field before plants have emerged. Application of the aqueous ionic solutions of metal alkanoates in such cases is typically tied to a scheduled application of the liquid fertilizer. However, fertilizers are generally not broadcast sprayed after plants have emerged because of the fertilizers tend to cause substantial damage to the crops by burning the leaves. Instead, fertilizers added postemergence are generally applied directly to the soil using drip, injection and side dressing methods.

One agricultural crop additive of the class of ammoniacal ionic solutions of zinc carboxylates described herein is commercially available under the ACA™ Concentrate 15-0-0 trade mark from Platte Chemical Company of Fremont, Nebr. ACA™ Concentrate 15-0-0 is currently available as a liquid containing 15% by weight ammoniacal nitrogen and 17% by weight zinc. ACA™ concentrate 15-0-0 is typically applied at a rate of ⅓ pint to ⅔ pint per acre. It is the application of the solution at such low rates which is generally understood to require application of the alkanoate in conjunction with an anhydrous ammonia, water or nitrogen fertilizer carrier to the soil by preemergent broadcast spraying, pre- or postemergent injection means, or post emergent drip means or side dressing.

It is against this background that the significant improvements and advancements of the present invention have taken place.

OBJECTS OF THE INVENTION

It is the principal object of the present invention to minimize deleterious effects of herbicide application to crops, such as leaf and plant tissue damage and plant stunting.

It is a further object of the present invention to apply an aqueous ammoniacal ionic solution of metal alkanoates to postemergent crops in a new manner.

It is a yet further object of the present invention to accomplish the aforementioned objects in an efficient and economical manner without causing toxicity problems to crops.

SUMMARY OF THE INVENTION

In accordance with the major aspects of the present invention, a composition containing an aqueous ammoniacal ionic solution of metal alkanoates and a herbicide is disclosed. An effective amount of this composition is applied to crops by broadcast spraying.

The composition of the present invention preferably contains a commercially available herbicide, water and an aqueous ammoniacal ionic solutions of metal alkanoates containing alkanoates of from two to six carbon atoms, with acetate ions most preferred. Preferably, the aqueous ammoniacal ionic solutions metal alkanoates contain agriculturally acceptable metals selected from the group consisting of boron, calcium, copper, iron, magnesium, manganese, molybdenum, potassium, sodium and zinc, with zinc particularly preferred. The most preferred aqueous ammoniacal ionic solution of metal alkanoates with which the present invention may be practiced is an aqueous ammoniacal ionic solution of zinc acetate.

When the aforementioned composition is applied postemergence to plants, for example by broadcast spraying, the water/herbicide solution functions as a carrier medium for the aqueous ammoniacal ionic solution of metal alkanoates.

Utilizing the aforementioned composition and employing the aforementioned method results in effective prevention and control of weeds in soybeans and other cash crops with minimal leaf and plant tissue damage to the crops.

A more complete appreciation of the present invention and its scope can be obtained from understanding the following detailed description of presently preferred embodiments of the invention, and the appended claims.

DETAILED DESCRIPTION OF THE INVENTION

In accordance with the present application, it has been discovered that an improved composition for application to crops contains a herbicide with which is mixed an aqueous ammoniacal ionic solution of metal alkanoates. When this composition is applied to crops, leaf and plant tissue damage such as burning, shriveling and discoloration of leaves, is substantially minimized, while, weed growth is satisfactorily prevented or controlled.

The compositions and methods of the present invention preferably employ an aqueous ammoniacal ionic solution of metal alkanoates containing alkanoates of from two to six carbon atoms, acetate being the most preferred. Preferred metals include agriculturally acceptable metals selected from the group consisting of boron, calcium, copper, iron, magnesium, manganese, molybdenum, potassium, sodium and zinc, with zinc particularly preferred.

When applying an aqueous ammoniacal ionic solution of zinc acetate and herbicide composition of the present invention post emergence to soybean plants in accordance with the present invention, conventional broadcast spray techniques are utilized in which 10 to 20 gallons of an aqueous solution of the composition of the present invention is broadcast sprayed per acre. The proportion of herbicide in the final aqueous solution is generally dictated by the herbicide manufacturer's recommended application rate. Adjuvants, for example, nonionic surfactants, petroleum based crop oils, methylated seed oils, ammonium sulfate and/or urea/ammonium nitrate may also be added in accordance with the herbicide manufacturer's recommendations, to enhance the effectiveness of the herbicide. Conventional adjuvant amounts and combinations are typically provided by adjuvant and/or herbicide manufacturers.

The composition of the present invention is typically prepared in a tank mounted on conventional broadcast spray equipment such as a Spray Coupe manufactured by Melroe Company of Bismark, N.D. The tank is initially filled approximately half full with water. The desired amount of herbicide is added to the water in the tank. The desired amount of aqueous ammoniacal ionic solution of metal alkanoates is then added to the solution in the tank. Water is then added to fill the tank. The addition of the water and other constituents and hydraulic agitation promotes sufficient mixing to disperse the constituents evenly in solution in the tank. The solution is then broadcast sprayed over the postemergent crop, for example soybeans, at the desired rate.

Alternatively, when the solution to be broadcast sprayed is to contain adjuvants, such adjuvants are added to with the herbicide to the water before the ammoniacal ionic solution of metal alkanoates is added to the tank. It may also be desirable for the solution to be broadcast sprayed to contain other products, for example fertilizers. One adjuvant commonly added to herbicide sprays is ammonium sulfate. When ammonium sulfate is to be added to the solution to be broadcast sprayed, the ammonium sulfate is added to the tank before the ammoniacal ionic solution of metal alkanoates has been added and before the tank is filled with water.

In yet another alternative, an aqueous solution of a herbicide and an ammoniacal ionic solution of metal alkanoates is applied with water. The aqueous ammoniacal ionic solution of metal alkanoates is premixed with a fertilizer solution and added to the herbicide and water solution in the tank or reservoir from which the solution will be broadcast sprayed or otherwise applied.

As mentioned previously, aqueous ammoniacal ionic solutions of zinc acetate are preferred as a constituent of the composition of the present invention. Most preferably, such aqueous ammoniacal ionic solutions of zinc-acetate contain zinc in a range by weight of from 5% to 20%, with a concentration of approximately 17% by weight zinc most preferred. An aqueous ammoniacal ionic solution of zinc acetate having this preferred zinc concentration can be produced according to Example I below.

EXAMPLE I

A stock solution of ammonium acetate in aqueous ammonia was prepared by mixing 33.6 parts of glacial acetic acid with 48 parts of water followed by slow addition to the cooled mixture of 18.4 parts of commercial anhydrous liquid ammonia, while maintaining the temperature between 25° and 50° C. After cooling the solution to 10° C., 21.8 parts of zinc oxide were slowly added with stirring while maintaining the temperature below 25° C. The zinc oxide dissolved rapidly to afford a stock solution containing 17.5% weight percent zinc which had a pH of 11.4 and a specific gravity of 1.27.

Compositions embodying the present invention, each containing one or more herbicide and an aqueous ammoniacal ionic solution of zinc acetate made in accordance with Example I, were diluted with water and combined to obtain the solutions and application rates described below in Examples II through IX.

EXAMPLE II

The aqueous ammoniacal ionic solution of zinc acetate made according to Example I is mixed with Galaxy™ herbicide, water, and a conventional commercially available 28% nitrogen solution (28-0-0) of urea and ammonium nitrate to produce an aqueous solution, of which each 20 gallons contains: (1) 1 quart Galaxy® herbicide; (2) 2 quart 28% nitrogen solution; (3) 10 fluid ounces Example I solution; and (4) water to 20 gallons. This solution is broadcast sprayed at a rate of 20 gallons per acre.

EXAMPLE III

The aqueous ammoniacal ionic solution of zinc acetate made according to Example I is mixed with Galaxy™ and Poast Plus™ herbicides, water, and a conventional commercially available 28% nitrogen solution (28-0-0) of urea and ammonium nitrate to produce an aqueous solution, of which each 20 gallons contains: (1) 1 quart Galaxy® herbicide; (2) 1½ pint Poast Plus™ herbicide; (3) 2 quart 28% nitrogen solution; (4) 10 fluid ounces Example I solution; and (5) water to 20 gallons. The solution is broadcast sprayed at a rate of 20 gallons per acre.

EXAMPLE IV

The aqueous ammoniacal ionic solution of zinc acetate made according to Example I is mixed with Pursuit™ herbicide, water, a conventional commercially available 28% nitrogen solution (28-0-0) of urea and ammonium nitrate, and a nonionic surfactant to produce an aqueous solution, of which each 20 gallons contains: (1) 3 fluid ounces Pursuit® herbicide; (2) 1 quart 28% nitrogen solution; (3) ⅕ quart Activator 90™, a commercially available nonionic surfactant; (4) ⅔ pint Example I solution; and (5) water to 20 gallons. This solution is broadcast sprayed at a rate of 20 gallons per acre.

EXAMPLE V

The aqueous ammoniacal ionic solution of zinc acetate made according to Example I is mixed with Pursuit™ and Assure II™ herbicides, water, a conventional commercially available 28% nitrogen solution (28-0-0) of urea and ammonium nitrate, and a nonionic surfactant to produce an aqueous solution, of which each 20 gallons contains: (1) 4 fluid ounces Pursuit® herbicide; (2) 7 fluid ounces Assure II™ herbicide; (3) 1 quart 28% nitrogen solution; (4) ⅕ quart Activator 90™, a commercially available nonionic surfactant; (5) 10 fluid ounces Example I solution; and (6) water to 20 gallons. This solution is broadcast sprayed at a rate of 20 gallons per acre.

EXAMPLE VI

The aqueous ammoniacal ionic solution of zinc acetate made according to Example I is mixed with Pursuit™ and Fusion™ herbicides, Activator 90™ (a commercially available nonionic surfactant), an aqueous solution of 28% nitrogen containing urea and ammonium nitrate, and water to produce an aqueous solution, of which each 30 gallons contains: (1) 4 fluid ounces Pursuit® herbicide; (2) 4 fluid ounces Fusion™ herbicide; (3) 0.6 quart Activator 90™; (4) 3 quarts 28% nitrogen solution; (5) 10 fluid ounces Example I solution; and (6) water to 30 gallons. This solution is broadcast sprayed at a rate of 30 gallons per acre.

EXAMPLE VII

The aqueous ammoniacal ionic solution of zinc acetate made according to Example I is mixed with Pursuit™ and Cobra™ herbicides, Dispatch™ adjuvant and water to produce an aqueous solution, of which each 20 gallons contains: (1) 4 fluid ounces Pursuit® herbicide; (2) 4 fluid ounces Cobra™ herbicide; (3) 2½ pints Dispatch™ adjuvant; (4) 8 fluid ounces Example I solution; and (5) water to 20 gallons. This solution is broadcast sprayed at a rate of 20 gallons per acre.

EXAMPLE VIII

The aqueous ammoniacal ionic solution of zinc acetate made according to Example I is mixed with Classic™, Pinnacle™ and Assure II™ herbicides, ammonium sulfate and water to produce an aqueous solution, of which each 20 gallons contains: (1) ¼ ounce Classic™ herbicide; (2) ¼ ounce Pinnacle™ herbicide; (3) 7 fluid ounces Assure II™ herbicide; (4) 2.0 pounds ammonium sulfate; (5) 8 fluid ounces Example I solution; and (6) water to 20 gallons. This solution is broadcast sprayed at a rate of 20 gallons per acre.

EXAMPLE IX

The aqueous ammoniacal ionic solution of zinc acetate made according to Example I is mixed with Pursuit™ herbicide, water, a conventional commercially available 28% nitrogen solution (28-0-0) of urea and ammonium nitrate, and a nonionic surfactant to produce an aqueous solution, of which each 20 gallons contains: (1) 4 fluid ounces Pursuit® herbicide; (2) 1 quart 28% nitrogen solution; (3) ⅕ quart Activator 90™, a commercially available nonionic surfactant; (4) 10 fluid ounces Example I solution; and (5) water to 20 gallons. This solution is broadcast sprayed at a rate of 20 gallons per acre.

Compositions of the present invention containing various combinations of herbicide(s) and ammoniacal ionic solution of zinc acetate of Example I were broadcast sprayed over soybean plants, postemergence but before appearance of blossoms, using conventional broadcast spray techniques. The acreage so sprayed is referred to herein as test acreage. Check acreage of soybean plants were broadcast sprayed with herbicide(s) solutions having the same herbicide concentration and application rate as the test acreage, but without addition of the ammoniacal ionic solution of Example I. Soybean yield in bushels per acre were determined for test acreage and check acreage. The results of eleven different tests are shown in Table II.

TABLE II

| Test No. | Herbicide | Composition and application rate | Soybean yield (bushel/acre) | | |
|---|---|---|---|---|---|
| | | | Herbicide with Example 1 sol'n | Herbicide only | Δ |
| 1 | Galaxy ™ | Example II | 44.6 | 38.6 | +6.0 |
| 2 | Galaxy ™ Poast Plus ™ | Example III | 30.5 | 28.1 | +2.4 |
| 3 | Pursuit ™ | Example IV | 43.0 | 44.7 | −1.7 |
| 4 | Pursuit ™ Assure II ™ | Example V | 43.7 | 41.4 | +2.3 |
| 5 | Pursuit ™ Fusion ™ | Example VI | 54.5 | 51.6 | +2.9 |
| 6 | Pursuit ™ Fusion ™ | Example VI | 56.0 | 47.0 | +9.0 |
| 7 | Pursuit ™ Cobra ™ | Example VII | 46.4 | 44.3 | +2.1 |
| 8 | Classic ™ Pinnacle ™ Assure II ™ | Example VIII | 42.7 | 40.5 | +2.2 |
| 9 | Pursuit ™ | Example IX | 58.4 | 52.9 | +5.5 |

The data shown in Table II indicates that on average, farmers obtained an increased yield of 3.4 bushels per acre of soybeans on test acreage to which a composition containing the aqueous ammoniacal ionic solution of zinc acetate of Example I and one or more herbicides was applied, as compared to check acreage to which only the herbicide(s) was applied.

Most unexpectedly, the leaf damage to the soybean plants from application of Galaxy™ herbicide was substantially reduced. When the check acreage fields were viewed from a distance, much of the check acreage crops appeared brown. In contrast, the test acreage to which the composition containing the aqueous ammoniacal ionic solution of zinc acetate of Example I and the Galaxy™ herbicide were applied appeared generally green and healthy looking.

The one test summarized in Table II in which soybean yield for check acreage was greater than for acreage in which an Example I solution and herbicide was applied (Test 3) had observable weed control problems.

In another test, the effect on leaf damage relating to herbicide application was quantified. Postemergent soybean plants were sprayed with a composition containing the aqueous ammoniacal ionic solution of zinc acetate of Example I mixed with Galaxy™ herbicide at the following rates:

2 pts Galaxy™/acre=standard application rate;

4 pts Galaxy™/acre=2 times standard rate; and 8 pts Galaxy™/acre=4 times standard rate.

In each case, the solution of Example I was applied at a rate of 10.7 oz/acre. Control tests were also conducted in which the above application rates for Galaxy™ herbicide were maintained, to which no Example I solution was applied. Data obtained two days after spraying in shown in Table III.

TABLE III

| Solution | Herbicide application rate 2 pints/acre | Herbicide application rate 4 pints/acre | Herbicide application rate 8 pints/acre |
|---|---|---|---|
| Galaxy ™ only | 32% leaf tissue damage | 38% leaf tissue damage | 42% leaf tissue damage |
| Galaxy + Example 1 Sol'n | 5% leaf tissue damage | 18% leaf tissue damage | 25% leaf tissue damage |

As can be seen from the data in Table III, at standard application rate for Galaxy™ herbicide, most of the leaf tissue damage was prevented by addition of the Example I solution of an aqueous ammoniacal ionic solution of zinc acetate. At herbicide application rates of two times (2×) and four times (4×) standard application rates, leaf tissue damage was substantially reduced.

The effect of the addition of the aqueous ammoniacal ionic solution of zinc acetate of Example I on the effectiveness of the Galaxy™ herbicide was tested. Visual ratings of weed control on a scale of 30 to 100 were made for each of three weeds (velvetleaf, common lambsquarter, and redroot pigweed) on the 3rd, 7th and 10th days after broadcast spray application of the composition of Example II above and on a check solution containing no Example I solution. Data obtained is summarized in Table IV.

TABLE IV

| Weed Evaluated | Solution | Day 3 | Day 7 | Day 10 |
|---|---|---|---|---|
| Velvetleaf | Galaxy ™ only | 90 | 100 | 100 |
| | Galaxy + Example I Sol'n | 70 | 100 | 100 |
| Common lambsquarter | Galaxy ™ only | 90 | 100 | 100 |
| | Galaxy ™ + Example I Sol'n | 70 | 95 | 100 |
| Redroot pigweed | Galaxy ™ only | 68 | 85 | 95 |
| | Galaxy ™ + Example I Sol'n | 37 | 75 | 91 |

As may be seen in Table IV, satisfactory weed control ratings of 90 or above for all three weeds measured were achieved by the 10th day after application with both the Galaxy™ herbicide check solution and the Galaxy™/aqueous ammoniacal ionic solution of zinc acetate of Example I. Although on the 3rd day, the composition of Galaxy™/aqueous ammoniacal ionic solution of zinc acetate of Example I lagged in weed control as compared to the soil to which the Galaxy™ herbicide check solution had been applied, by the 7th day, weed control was proceeding satisfactorily for all solutions.

Presently preferred embodiments of the present invention and many of its improvements have been described with a degree of particularity. It should be understood that this description has been made by way of preferred examples, and that the invention is defined by the scope of the following claims.

What is claimed is:

1. A method of reducing crop damage resulting from application of a herbicide, said method comprising the step of:

applying postemergence to crops a composition containing:
        an effective amount of a herbicide having an active ingredient selected from the group consisting of quizalofop, sodium salt of bentazon, sodium salt of acifluorfen, chlorimuron ethyl, lactofen, fluazifop-p- butyl, fenoxaprop-ethyl, methyl 3-[[[[4-methoxy-6-methyl-1,3,5-triazin-2-yl]amino]carbonyl]amino]sulfonyl]2-thiophenecarboxylate, 2-[1ethoxyimon]butyl]5-[2-[ethylthio]propyl]-3-hydroxy-2-cyclohexene-1-one, and ammonium salt of imazethapyre; and an effective amount of an aqueous ammoniacal ionic solution of zinc alkanoates each comprising from 2 to 6 carbon atoms.

2. The method of claim 1 wherein the aqueous ammoniacal ionic solution of zinc alkanoates contains from 5% to 20% by weight zinc.

3. The method of claim 2 wherein the aqueous ammoniacal ionic solution of zinc acetate is applied at a rate of from ⅓ pint to ⅔ pint per acre.

4. A method of reducing crop damage resulting from application of a herbicide, said method comprising the step of applying postemergence to crops a composition comprising:

an effective amount of a herbicide having an active ingredient selected from the group consisting of quizalofop, sodium salt of bentazon, sodium salt of acifluorfen, chlorimuron ethyl, lactofen, fluazifop-p-butyl, fenoxaprop-ethyl, methyl 3-[[[[4-methoxy- 6-methyl-1,3,5-triazin-2-yl]amino]carbonyl]amino]sulfonyl]2-thiophenecarboxylate, 2-[1-ethoxyimon]butyl]-5-[2-[ethylthio]propyl]-3-hydroxy-2-cyclohexene- 1-one, and ammonium salt of imazethapyre; and an effective amount of an aqueous ammoniacal ionic solution of metal alkanoates, wherein said metal is selected from the group consisting of zinc and magnesium, and said alkanoates contain from 2 to 6 carbon atoms.

5. A method of reducing crop damage resulting from application of a herbicide, said method comprising the steps of:

broadcast spraying postemergent crops with an effective amount of a composition containing an effective amount of a herbicide having an active ingredient selected from the group consisting of quizalofop, sodium salt of bentazon, sodium salt of acifluorfen, chlorimuron ethyl, lactofen, fluazifop-p-butyl, fenoxaprop-ethyl, methyl 3-[[[[4-methoxy-6-methyl-1,3,5-triazin-2-yl]amino]carbonyl]amino]sulfonyl]2-thiophenecarboxylate, 2-[1-ethoxyimon]butyl]-5-[2-[ethylthio]propyl]-3-hydroxy 2-cyclohexene-1-one, and ammonium salt of imazethapyre, and an effective amount of an aqueous ammoniacal ionic solution of metal alkanoates, wherein said metal is selected from the group consisting of zinc and magnesium and wherein said alkanoates contain from 2 to 6 carbon atoms.

6. The method of claim 5 wherein the aqueous ammoniacal ionic solution of metal alkanoates is an aqueous ammoniacal ionic solution of zinc acetate.

7. The method of claim 6 wherein the aqueous ammoniacal ionic solution of zinc acetate contains from 5% to 20% by weight zinc.

8. The method of claim 7 wherein the aqueous ammoniacal ionic solution of zinc acetate is applied at a rate of from ⅓ pint to ⅔ pint per acre.

9. A method of reducing crop damage resulting from application of a herbicide, said method comprising the step of applying postemergence to crops a composition comprising:

an effective amount of a herbicide containing a sodium salt of bentazon and a sodium salt of acifluorfen; and an effective amount of an aqueous ammoniacal ionic solution of zinc alkanoates.

10. The method of reducing crop damage according to claim 9, wherein said composition further includes an effective amount of a non-ionic surfactant.

11. The method of reducing crop damage according to claim 9, wherein said composition further includes an effective amount of an aqueous fertilizer solution containing approximately 28% by weight nitrogen.

12. A method of reducing crop damage resulting from application of a herbicide, said method comprising the step of applying postemergence to crops a composition comprising:

an effective amount of a herbicide containing chlorimuron ethyl; and an effective amount of an aqueous ammoniacal ionic solution of zinc alkanoates.

13. The method of reducing crop damage according to claim 12, wherein said composition further includes an effective amount of a non-ionic surfactant.

14. The method of reducing crop damage according to claim 12, wherein said composition further includes an effective amount of an aqueous fertilizer solution containing approximately 28% by weight nitrogen.

15. A method of reducing crop damage resulting from application of a herbicide, said method comprising the step of applying postemergence to crops a composition comprising:

an effective amount of a herbicide containing an ammonium salt of imazethapyre; and an effective amount of an aqueous ammoniacal ionic solution of zinc alkanoates.

16. The method of reducing crop damage according to claim 15, wherein said composition further includes an effective amount of a non-ionic surfactant.

17. The method of reducing crop damage according to claim 15, wherein said composition further includes an effective amount of an aqueous fertilizer solution containing approximately 28% by weight nitrogen.

* * * * *